(12) United States Patent
Agapiou et al.

(10) Patent No.: US 8,054,460 B2
(45) Date of Patent: Nov. 8, 2011

(54) METHODOLOGY FOR EVALUATING THE START AND PROFILE OF A THREAD WITH A VISION-BASED SYSTEM

(75) Inventors: John S. Agapiou, Rochester Hills, MI (US); Michael E. Swanger, Almont, MI (US); Daniel K. Owusu, Grand Blanc, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 419 days.

(21) Appl. No.: 12/432,548

(22) Filed: Apr. 29, 2009

(65) Prior Publication Data

US 2009/0279083 A1    Nov. 12, 2009

Related U.S. Application Data

(60) Provisional application No. 61/052,309, filed on May 12, 2008.

(51) Int. Cl.
*G01N 21/00* (2006.01)
(52) U.S. Cl. .................................... 356/241.1
(58) Field of Classification Search ........................ None
See application file for complete search history.

(56) References Cited

U.S. PATENT DOCUMENTS

| 5,610,994 | A | 3/1997 | Stadtfeld et al. |
| 6,703,831 | B1* | 3/2004 | Keely et al. .................. 324/232 |
| 7,187,784 | B2 | 3/2007 | Tawfiq et al. |
| 7,266,420 | B2 | 9/2007 | Budd |

FOREIGN PATENT DOCUMENTS

KR       10-0467080 B1    1/2005
* cited by examiner

*Primary Examiner* — Tu Nguyen
(74) *Attorney, Agent, or Firm* — John A. Miller; Miller IP Group, PLC

(57) ABSTRACT

A system and method for identifying the start location of the lead thread and the thread profile and quality in a threaded bore in a part, where the system and method can be used for determining the location of the lead thread in a threaded bore in a cylinder head for a spark plug in one non-limiting embodiment. The system includes a moveable table on which the part is mounted. The system also includes a probe having an optical assembly that is inserted in the threaded bore. A camera uses the optical assembly to generate images of the thread bore, where the images are image slices as the probe moves through the threaded bore. The image slices are unwrapped and then joined together to form a planer image to determine a start location of the lead thread, thread count, defects in the threaded bore and thread profile parameters.

19 Claims, 9 Drawing Sheets

METHODOLOGY FOR EVALUATING THE START AND PROFILE OF A THREAD WITH A VISION-BASED SYSTEM

CROSS-REFERENCE TO RELATED APPLICATIONS

This application claims the benefit of the priority date of U.S. Provisional Patent Application Ser. No. 61/052,309, titled Methodology for Evaluating the Start and Profile of a Thread with a Vision-Based System, filed May 12, 2008.

BACKGROUND OF THE INVENTION

1. Field of the Invention

This invention relates generally to a system and method for determining a thread profile, such as the angular position of the lead thread, standard thread characteristics, and thread defects in a threaded bored, and, more particularly, to a system and method for determining the starting location of the lead thread in a threaded bore, for example, in a cylinder head for a vehicle so that an end of a spark plug threaded into the bore has a desired rotational angle in the cylinder, where the system is a vision-based system.

2. Discussion of the Related Art

As a critical application in the art, a cylinder head for a vehicle is typically an aluminum structure that includes threaded bores that accept spark plugs in a threaded engagement so that an end of the spark plug is properly oriented in the cylinders of the vehicle engine. A vehicle design considers many things including engine performance. One area that provides improved engine performance for a certain engine design includes providing a proper rotational orientation of the spark plug within the cylinder that will provide the best fuel economy. In order to provide the proper rotational orientation of a spark plug, the threaded bore that the spark plug is threaded into needs to be tightly controlled so that when the spark plug is threaded into the bore the rotational orientation of the spark plug is at the desired location. In order to accomplish this goal, it is necessary to know the location of the lead thread in the threaded bore so that when the spark plug is threaded into the bored, it stops at the proper location.

There is presently no method and/or apparatus for a standard manufacturing procedure to identify and determine the location of the start of the lead thread in a threaded hole. A manual visual inspection process can be used including using a rigid or flexible borescope. Manual borescopes are very slow, are subject to human visual performance and can only be used for periodic checks to verify the start thread when parts are found defective after assembly.

SUMMARY OF THE INVENTION

In accordance with the teachings of the present invention, a system and method are disclosed for identifying the start location of the lead thread and thread profile and quality in a threaded bore in a part, where the system and method can be used for determining the location of the lead thread in a threaded bore in a cylinder head for a spark plug in one non-limiting embodiment. The system includes a moveable table on which the part is mounted. The system also includes a probe having an optical assembly that is inserted in the threaded bore. A camera uses the optical assembly to generate images of the thread bore, where the images are image slices as the probe moves through the threaded bore. The image slices are unwrapped and then joined together to form a planer image that is used to determine the start location of the lead thread, thread count, thread depth, defects in the threaded bore and thread profile parameters.

Additional features of the present invention will become apparent from the following description and appended claims, taken in conjunction with the accompanying drawings.

DETAILED DESCRIPTION OF THE EMBODIMENTS

Figure 1:
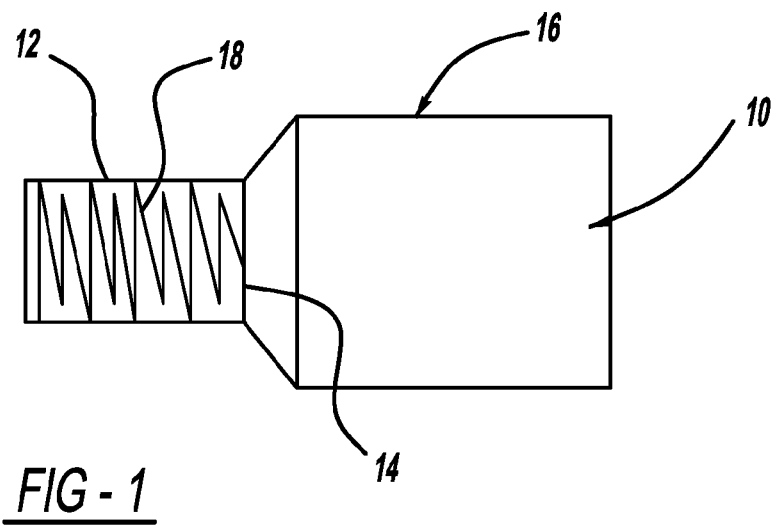
FIG. 1 is a plan view of a threaded bore in a cylinder head.

The following discussion of the embodiments of the invention directed to a system and method for identifying the location of the lead thread in a threaded bore and inspecting the threaded bore for thread damage is merely exemplary in nature, and is in no way intended to limit the invention or its applications or uses.

The present invention proposes a system and method for inspecting a threaded bore to determine the start location of the lead thread and to inspect the threads for damage or profile errors. The inspection process employs a high resolution, high-speed, vision-based system and related process that inspect the threads in the threaded bore. Based on scanned images obtained from a camera, the system can identify the location of the lead thread and the aforementioned thread attributes. An in-line implementation requires a methodology to analyze data from the surface of the threads, with the internal or external threaded images, creating a surface topography at the entrance or along the full threaded profile depending on the objectives. For example, the identification of the start location of the lead thread requires only a scan of the first few threads. The full threaded section is acquired only if the evaluation of all the threads is desired, such as looking for defects and profile parameters, such as thread pitch, crest width, root width, thread height, flank face, etc. More specifically, the measurement of the thread height requires a Stitch-Modulated "Interferograms" method. An in-line inspection machine with three axes of motion that utilizes a vision system and a specified script methodology is employed for this purpose in one embodiment.

The methodology of the invention will estimate the location (angular position) of the start of the lead thread and it will then define the starting thread with respect to a specified zero bore orientation (e.g. 120 degrees from the zero position) or four rotational quadrants in the threaded bore. One non-limiting application for this methodology is the orientation of spark plugs for engines. The present invention eliminates the risk of generating a bad thread or identifying the wrong start thread orientation.

As will be discussed in detail below, the disclosed methodology may require the following integrated hardware and software in a non-contact vision system. An ultra-high resolution digital camera and customized lens and LED lighting for small bores; an image acquisition system; software and customized graphical user interface per initial GMPT specifications for routine editing and output statistical review using generic software available in the market; a customized image processing script using a standard image processing library and software (e.g. LABVIEW Image Assistant), an integrated inspection station, conveyors and shuffling automation; a station including a unique single or multi-axis table including a robot, and feedback control system for in-line optimization of the lead thread location.

FIG. 1 is an illustration of a spark plug hole 10 in a cylinder head 16 for a vehicle, where the spark plug hole 10 includes a threaded bore 12. As will be discussed in detail below, the present invention determines the start location 14 of the thread 18 so that when the spark plug is threaded into the bore 12, the rotational orientation at an end of the spark plug is at a desirable location within the vehicle cylinder to provide the desired vehicle performance and fuel economy for a particular engine design. The system and method of the invention can perform the threaded bore evaluation at current manufacturing line rates, can improve the quality control, will provide standardized data back to the product and manufacturing engineers for optimization and provide continuous improvement activities of oriented spark plug applications.

Figure 2A:
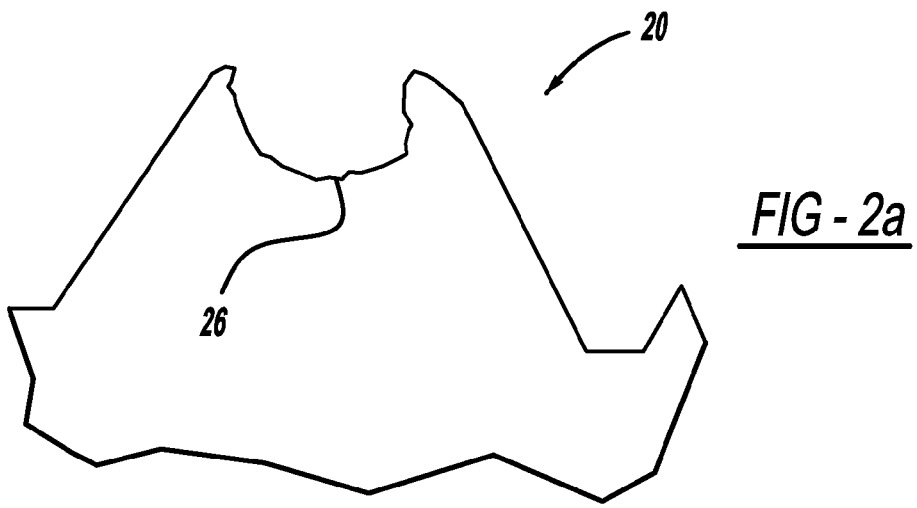
FIGS. 2(a) and 2(b) are cross-sectional views of a thread including a defect and no-defect, respectively.
Figure 2B:
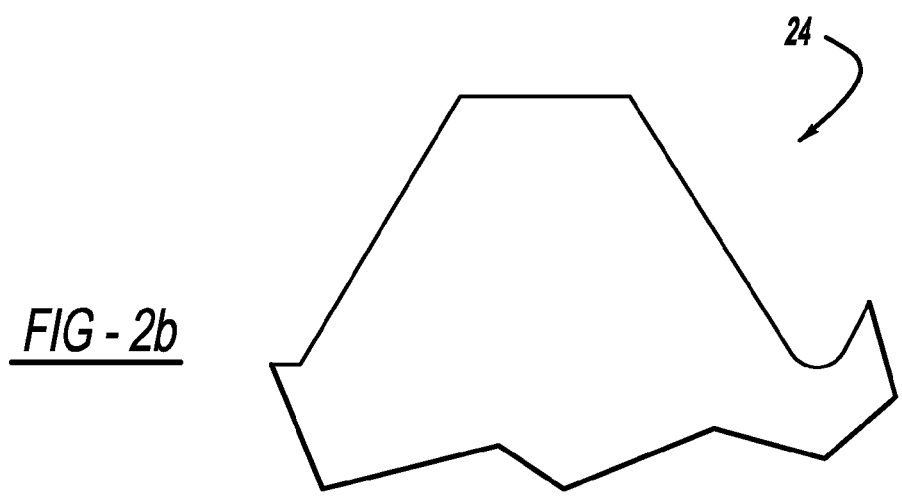

FIG. 2(a) is a cross-sectional view of a thread 20 in a threaded bore including a defect 26 and FIG. 2 (b) is a cross-sectional view of a thread 24 in a threaded bore with no defects.

Figure 3:
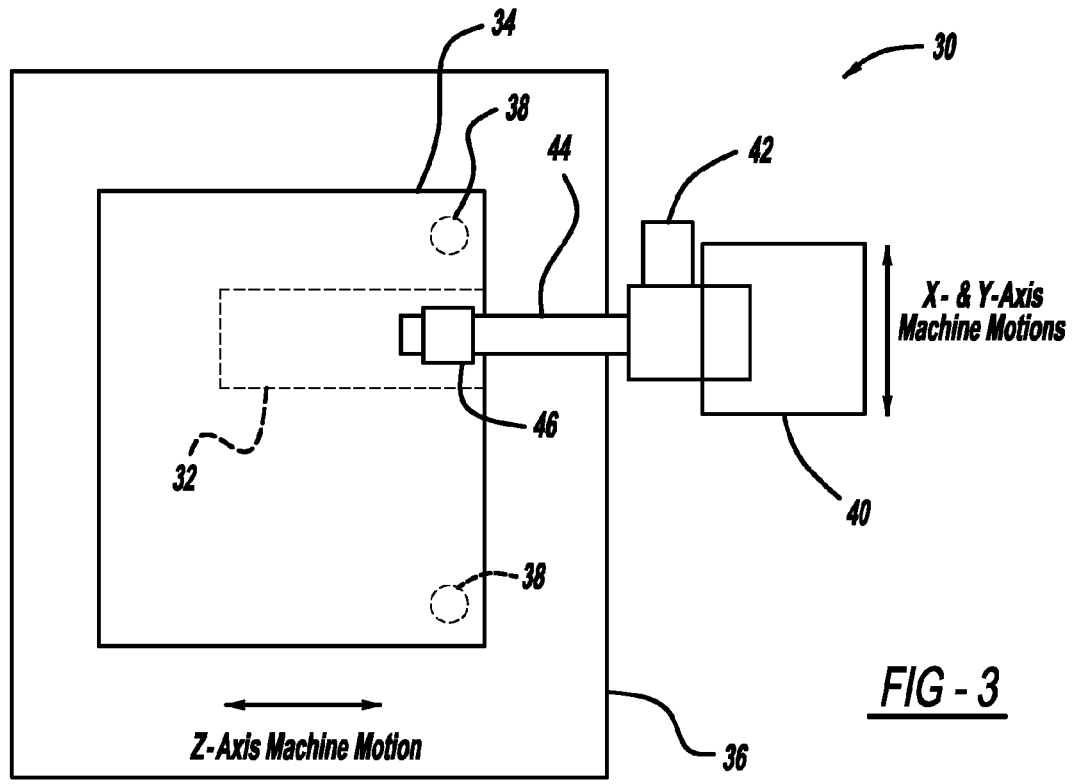
FIG. 3 is a plan view of a system for providing a vision-based inspection of a threaded bore, according to an embodiment of the present invention.

FIG. 3 is a plan view of an automated inspection system 30 for taking images of a threaded bore 32 in a part 34. The part 34 is mounted to a machine stage 36 that moves in the Z-axis direction, where the part 34 is fixed to the stage 36 using part locators 38. The system 10 includes a tool-holder 40 that moves in the X-axis and the Y-axis direction and is part of a CNC machine. An ultra-high resolution camera 42 is mounted to the tool-holder 40, and a probe 44 is mounted to the camera 42. A lens and light optical assembly 46 is provided at an end of the probe 44 opposite to the tool-holder 40, and is inserted into the threaded bore 32 to take images of the bore 32.

The part 34 is presented to and from the thread inspection station using a single or multi-axis dedicated or CNC automation. The probe 44 is inserted in the bore 32 as an introduced product in a fixture to scan an image of the bore's internal surface. The automated system 30 has the capability to insert the probe 44 in a specified threaded bore in the part using a CNC program. In addition, the system 30 may have the capability to perform circular interpolation around the bore 32 or external threads using two and/or three axes interpolation in order to 'see' the entire circumference of the perimeter of the bore section. The image collection from the bore 32 using the ultra-high resolution (UHR) camera 40 coupled to the extended lens and light optical assembly 46 results in an image in annular view. Other similar systems, such as a Sight-Pipe using internal axial mirrors or conical mirrors, can be used at the probe 44 to capture the images of the bore surface.

The region of interest (ROI) is established, i.e., between indicated rings 202, using a Labview image processing tool, or another comparative system, known to those skilled in the art. The ROI is sampled at the optimal depth of view at the bore surface. This may require a different probe for different bore sizes if the ability to focus on the different bore diameters cannot be automatically adjusted or re-calibrated.

The system 30 is designed around the probe 44. Off axis low angle illumination is desirable for finding the crest of the threads. The two edges of the thread crest are used to determine the location of the basic crest. Likewise, the thread root location and pitch consistency will be evaluated. Defective threads will be identified for quality control.

The location of the optical assembly 46 relative to the bore 32 is critical. For this reason, the part to be measured is located in a fixture using a 3-2-1 locating scheme to reduce the variability between the probe 44 and the bore's center location. A special pilot alignment is used by evaluating the image at the entry and bottom of the hole or the entrance and the crest of a thread further in the hold depth and performing an automatic alignment of the probe 44 using the X- and Y-axis under the head. This will require some flexibility of the probe 44 in the tool-holder 40 to compensate for concentricity differences between the probe 44 and the bore 32.

The Z-axis of the automated system 30 can utilize a glass scale linear encoder in the slide to precision control the motion of the probe 44 in the bore 32 for triggering the camera 42 properly. The image processing methodology consists of separating every height change on the surface using an image processing software script. Numerous images are collected as the collecting lens assembly 46 traverses the length of the bore 32. The most critical section is the entry of the bore 32 in this case. The camera 42 is triggered by a linear encoder, glass scale system. All collected images are buffered. The ROI is extracted from each of the collected images using the Labview image processing tool. Each circular element of the image is buffered. In addition, each circular element of the image is "unwrapped" into a linear element using the Labview image processing algorithm and each of these linear elements is buffered. The collected images are "stitched" together in the Labview image processing tool if necessary for thread profile analysis.

Figure 4:
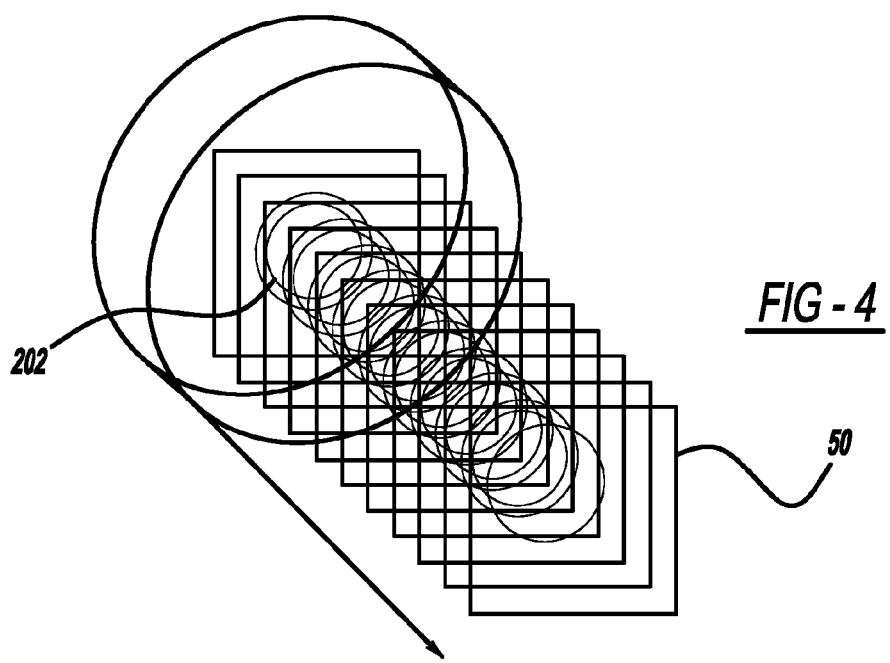
FIG. 4 is a representation of a plurality of slices of images produced by the machine shown FIG. 3 along a threaded bore.

FIG. 4 is a representation of a plurality of image slices 50 taken by the camera 40 in the bore 32. Particularly, as the stage 36 is moved in the z-axis when the probe 44 is within the bore 32, the camera 40 will take an image of the circumference of the bore 32 at that particular location producing a series of the image slices 50.

Figure 5:
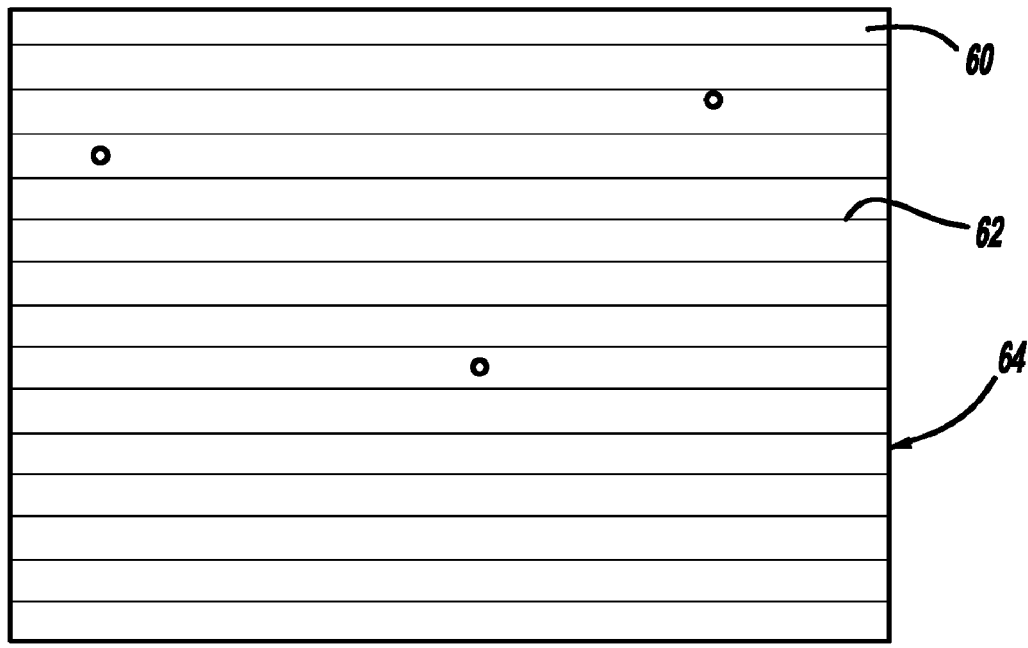
FIG. 5 is a plurality of linear images produced by the machine shown in FIG. 3 that have been stitched together.

FIG. 5 is an illustration of a plurality of unwrapped image elements 60 of a bore that have been stitched together along lines 62 to form a complete image 64 as discussed above. Particularly, each image element 64 is one of the image slices 50 that has been cut and un-rolled to be a planar element. The image 64 shown in FIG. 5 is generated through successive area scan images along the entire bore length of interest and all threads are captured. The final image is rendered and the contrast is balanced using an image processing tool.

Figure 6:
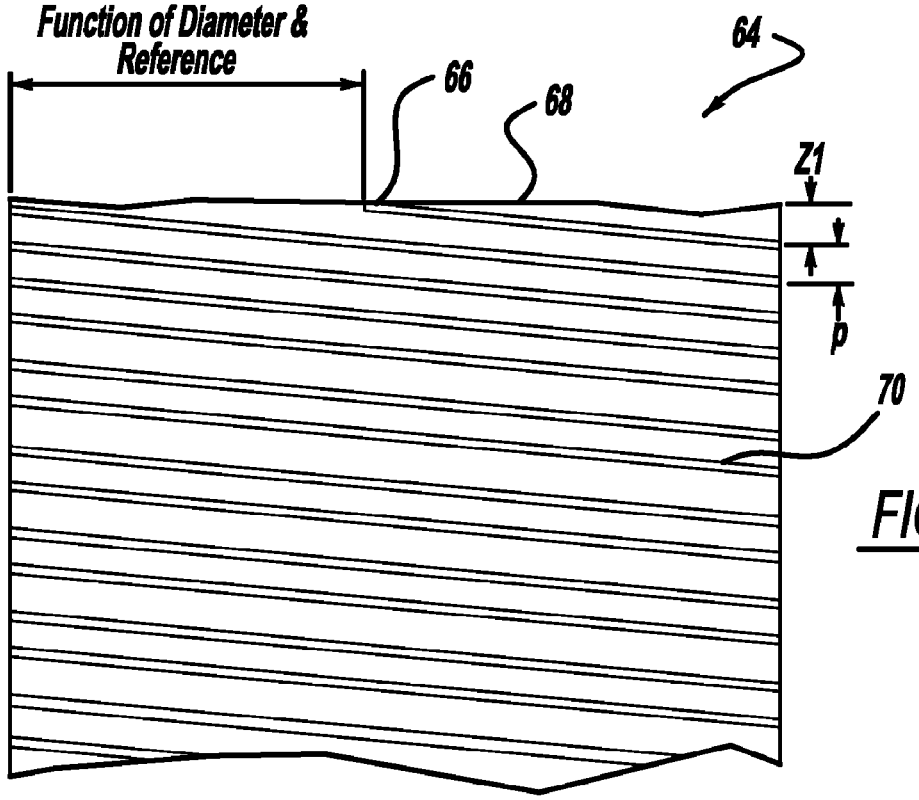
FIG. 6 is the plurality of linear images stitched together shown in FIG. 5 showing threads of the threaded bore.

All of the lines in the unwrapped image 64 are revealed and analyzed using a grayscale line analysis image processing tool. FIG. 6 shows the image 64 after thread lines 70 have been revealed using this analysis. The script consists of a series of imaging algorithms that isolate the thread lines 70 from the remaining image i.e., the bore surface. The start 66 of the lead thread can be identified by determining the lead thread intersection with the top surface 68 of the image 64. The script methodology for evaluating the start 72 of the lead thread and other thread features, such as pitch, pitch consistency among adjacent threads, thread height and defective or missing threads, can be shown.

Figure 7:
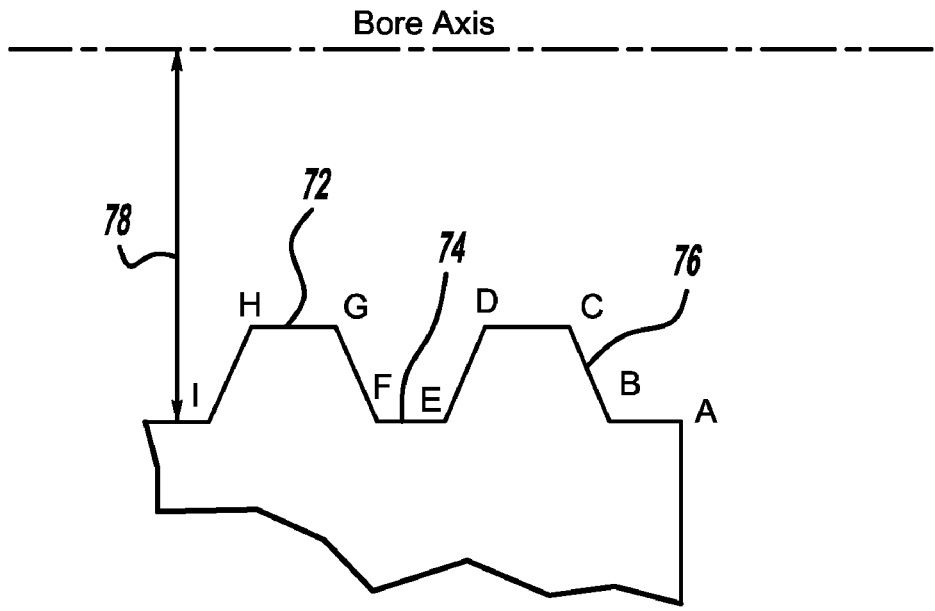
FIG. 7 is a cross-sectional view of a portion of a thread showing thread elevations.
Figure 8:
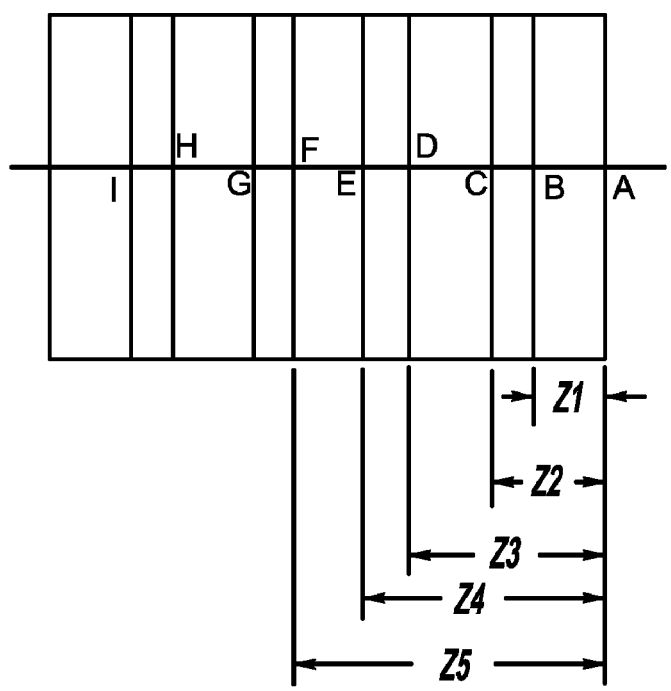
FIG. 8 is a planar representation of the cross-sectional view of the bore shown in FIG. 7.

FIG. 7 is a cross-sectional view of a portion of the image 64 showing crests 72, valleys 74 and transitions 76 therebetween of the threaded bore 32. The bore radius of the major diameter is identified by line 78. Each location of a transition to a different level is labeled with a letter A-I from a start surface of the bore. Each line is shown in a planar parallel view in FIG. 8 so that distances Z1-Z5 can be identified to determine the widths of the crest 72, the valleys 74 and the transitions 76 therebetween. Thus, the quality of the threads can be determined from the images.

The inspection system 30 can be used in-line after the threading station to provide feedback for the cutting tool and/or spindle Z-axis adjustments to improve the thread angular orientation relative to a reference. If the variation of the start thread orientation is within a specified tolerance, the process is completed. Otherwise, this information can be post-processed and used in the assembly for a class fit spark plug using the four quadrants approach. In addition, the information can be used to adjust the machine tool to cut the next thread at the specified orientation.

The support elements for in-line thread inspection are designed with a vision system and spindle Z-axis approach distance feedback. This represents an intelligent threading system. Using these wireless vision sensors provides flexibility and the information will be used to monitor the performance of the thread and its relationship to part quality. The tool length offset can be adjusted to control the start lead thread orientation/location.

Figure 9A:
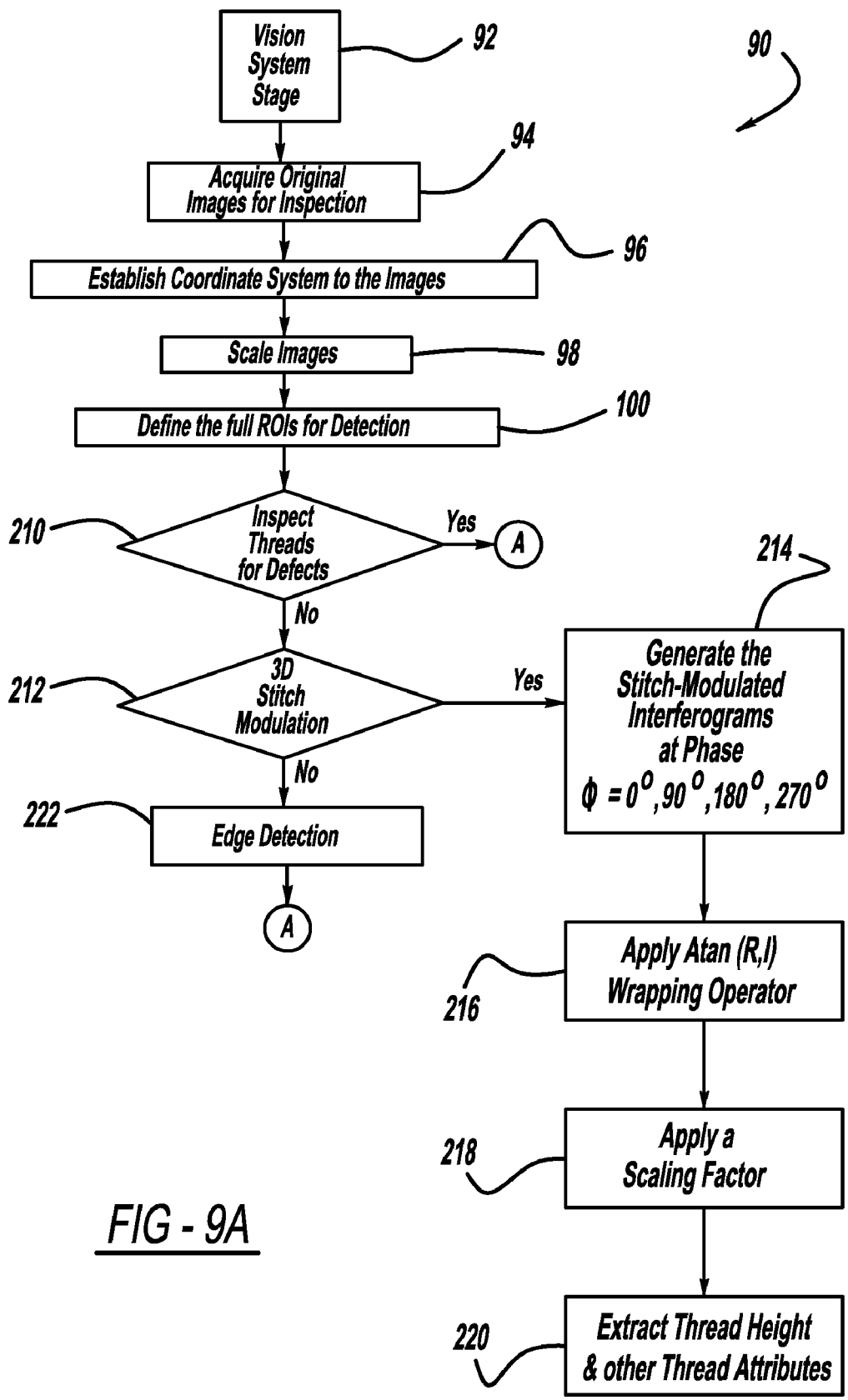
FIGS. 9A, 9B are flow chart diagrams showing a process for identifying thread defects and the start location of a lead thread in a threaded bore, according to an embodiment of the present invention.
Figure 9B:
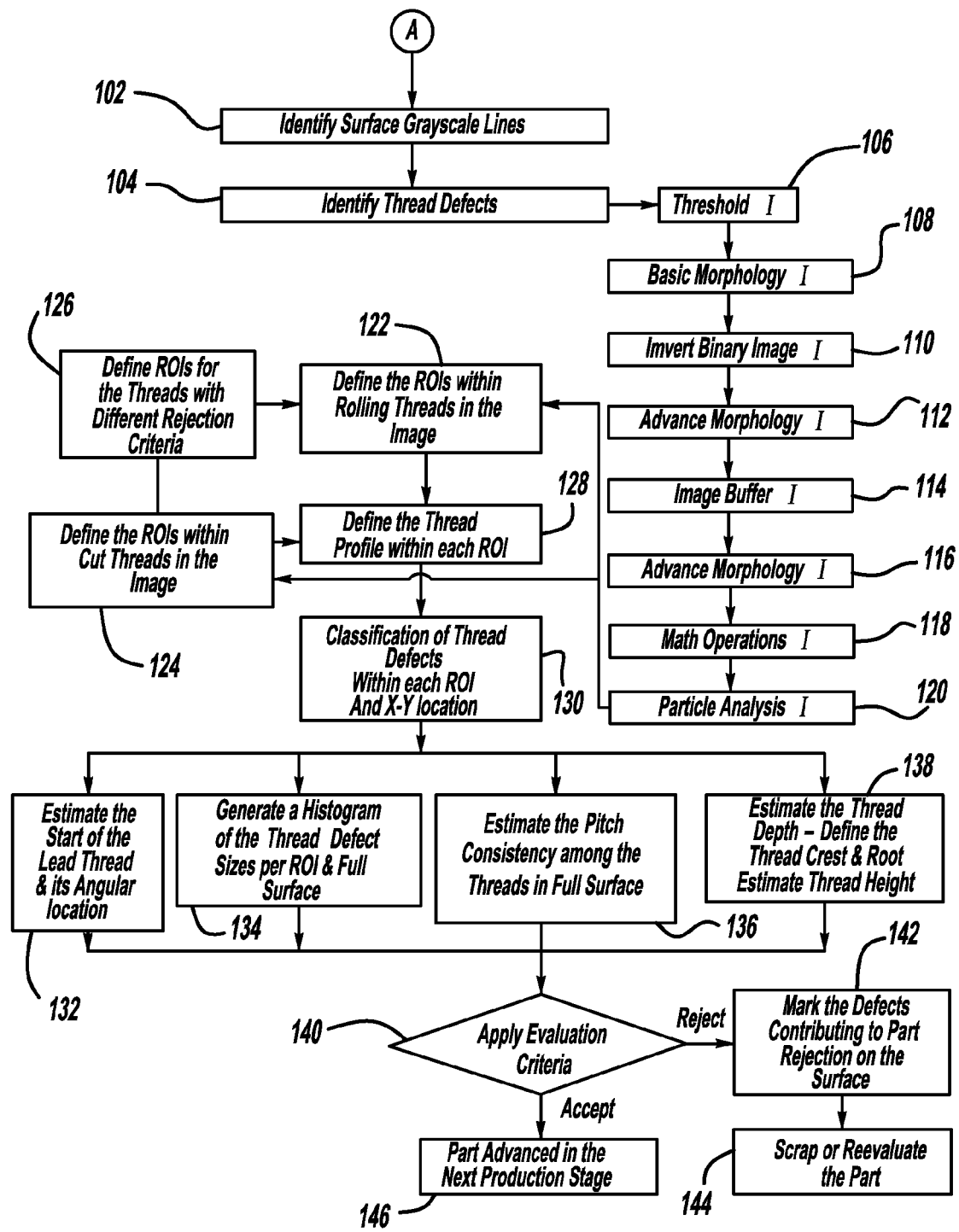

FIG. 9 is a flow chart diagram 90 showing a process for identifying thread defects and profile errors. The vision inspection system is initiated at box 92 and the images are acquired at box 94. This step acquires an image of the part surface as viewed through the camera 42. The camera 42 is synchronized with the linear encoder for triggering along the length of the bore 32. All the images are sectioned at the ROI, unwrapped and then switched together to generate the image of the full top surface of the bore 32. The analysis algorithm then establishes a coordinate system for the images at box 96, and the images are scaled at box 98. The algorithm then defines the region of interest for detection at box 100. In pre-selected regions of interest, a pattern recognition algorithm is used to locate known features on the image to establish an orientation, a scaling factor and a coordinate system that are all relative to the actual scanned surface.

The image is scaled to convert the pixel resolution to the actual work-piece units of measure. This is required in order to later define the location of the thread line and its intersection with the top surface of the bore. This is done by establishing a region of interest around an area of the image for which a search is performed for a specified range of thread lines with a pre-specified lead angle and pitch. The various regions of interest, in this case a start of the lead thread, can be scaled for angular position and specified relative to the previously defined coordinate system. Additional parameters can be determined, such as thread height, using the relative grayscale of the root and crest. The thread pitch p is also determined from the image by counting the edges of the surface transition, or the change in slope, as expected for a threaded section. Missing threads or defective threads can be identified by viewing the light bar.

The algorithm decides whether it needs to inspect the threads for defects at decision diamond 210, and if so, proceed to box 102 to identify the surface for gray scale lines. If the threads do not need to be inspected for defects at the decision diamond 210, then the algorithm determines whether a three-dimensional Stitch-Modulation needs to be performed at decision diamond 212.

Figure 10:
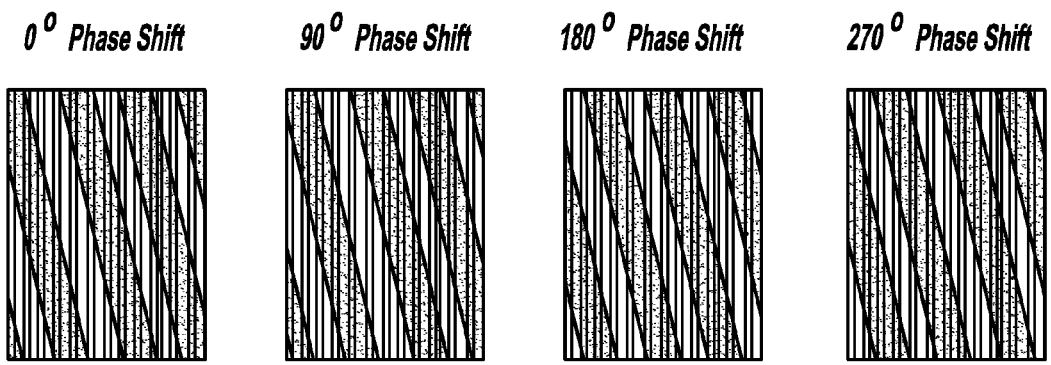
FIG. 10 shows Stitch-Modulated images sampled at a phase shift of 0°, 90°, 180° and 270°.
Figure 11:
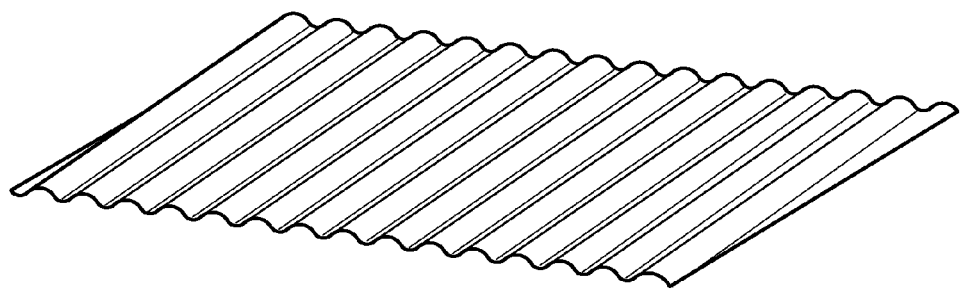
FIG. 11 shows a model for a thread profile using 15 threads that have been unrolled.

If a three-dimensional Stitch-Modulation does need to be performed, then the algorithm generates Stitch-Modulated interferograms for phase shifts of 0°, 90°, 180° and 270° at box 214. A quantitative approach to estimate the thread height is to form Stitch-Modulated "interferograms" and apply a arctangent "wrapping operator". In this case, the "axi-con" collector optics (allows for panoramic image collection) will travel along the threaded hole. Simultaneous to image collection the supporting light source will be modulated using a function generation technology and allowed generate a sinusoidal waveform at a know phase angle and magnitude. The resulting images will contain a fringe pattern of which the intensity values at each pixel which will range from 0 to $2^n$. For example, the "Stitch-modulated" images each simulated at a 90 degree phase shift are illustrated in FIG. 10 obtained from a model in FIG. 11 generated to a M15×1.5 UTS thread profile (assume 15 threads "Unrolled" from an internal diameter threaded hole). In addition, the diode-based light source at frequency f produces an intensity gradient that is proportional to the modeled thread height. The stitch-modulated images in FIG. 1 are shown with a shift of 0, 90, 180 and 270 degrees respectively.

Figure 12:
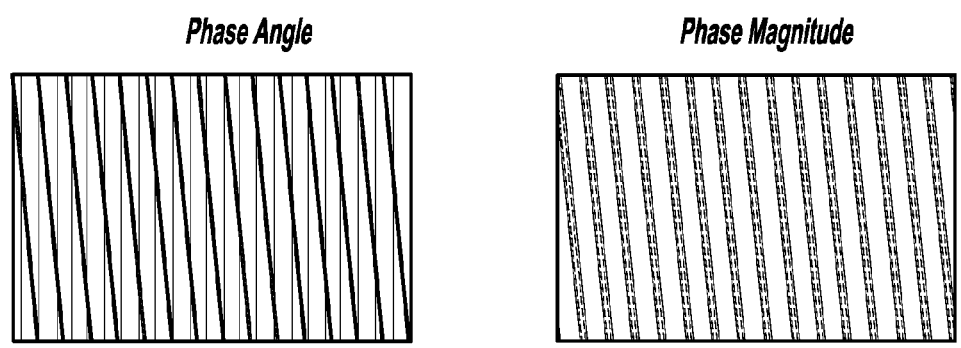
FIG. 12 shows the phase angle and the phase magnitude of the threads in the model shown in FIG. 11.
Figure 13A:
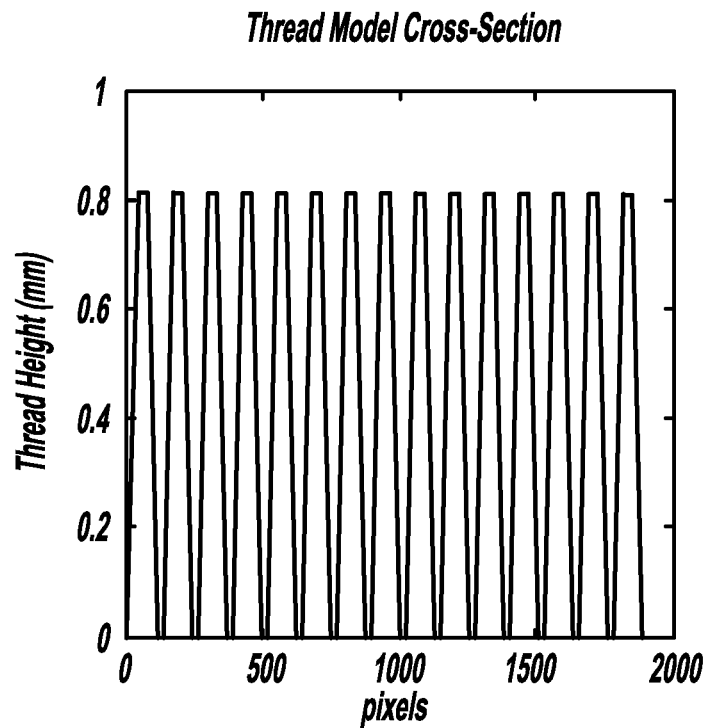
FIGS. 13A, 13B show a comparison of the measured and calculated thread height Z of the thread profile.
Figure 13B:
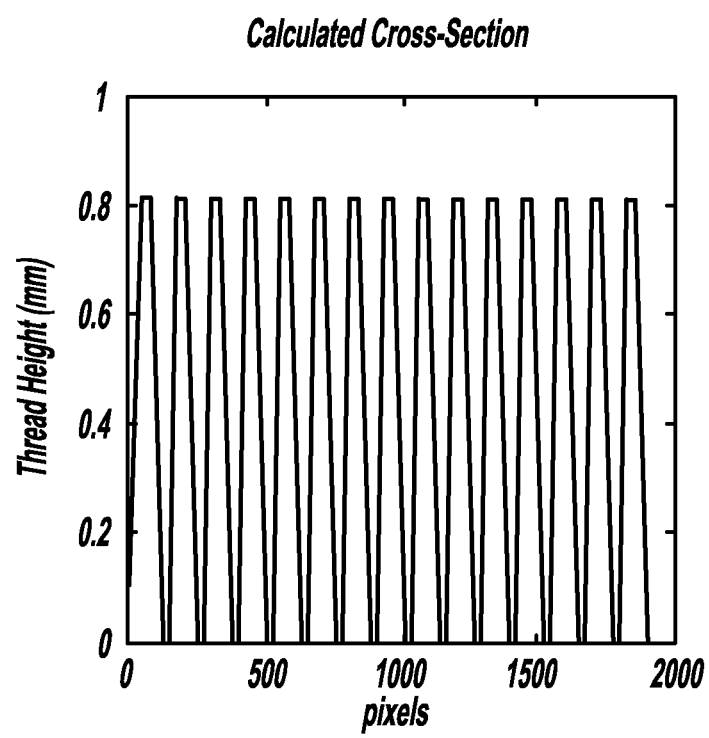
Figure 14:
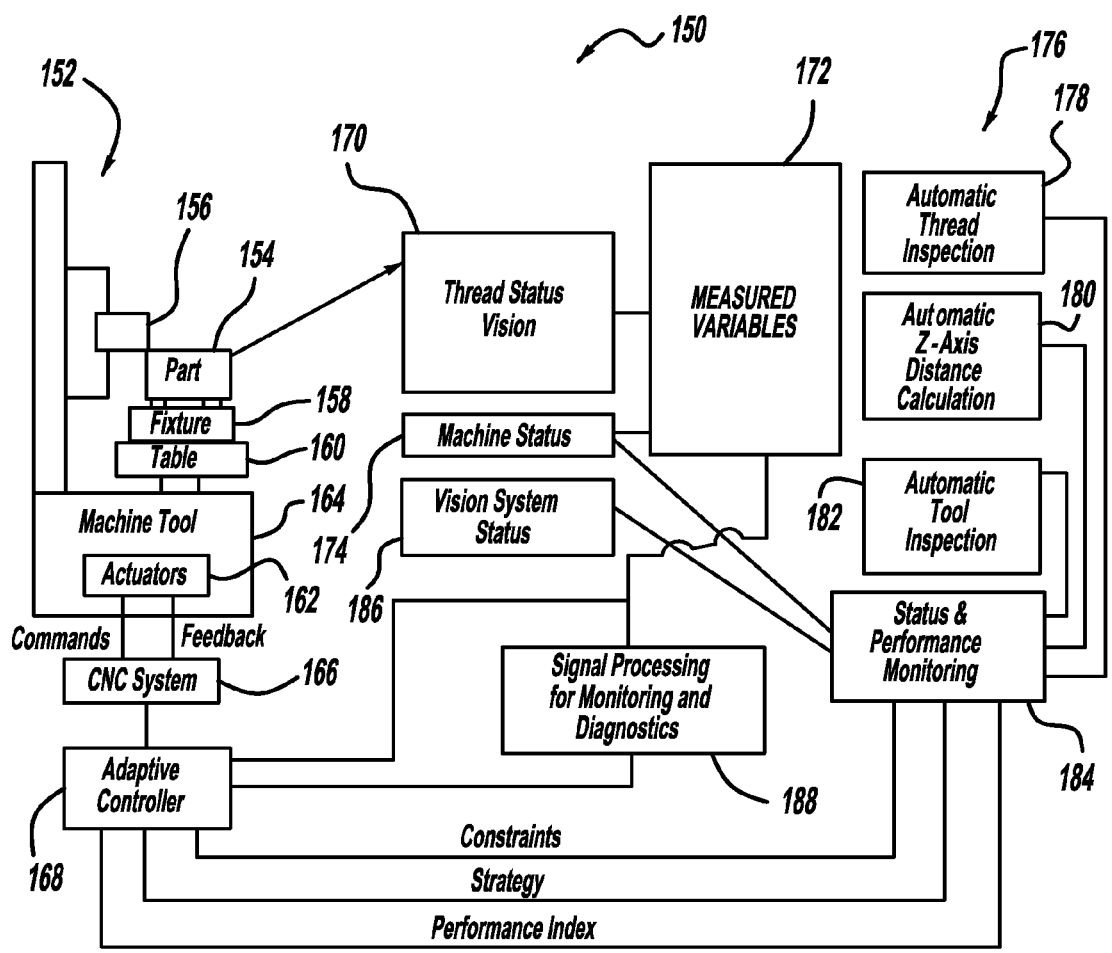
FIG. 14 is a block diagram of a control system for machining the threads and imaging the threads in a threaded bore.

The application defines the phase angle as the ATAN(R,I) wrapping operator at box 216, where $R=\Delta I_{31}$ and $I=\Delta I_{42}$, $\Delta I_{31}$ and $\Delta I_{42}$ are the per pixel intensity values of the images. Then approximate a phase magnitude as $(\Delta I_{31}^2+\Delta I_{42}^2)^{0.5}$. The phase angle and magnitude are shown in FIG. 12. For direct calculation of the interesting height Z of the thread profile, information gathered from the phase angle and/or phase magnitude is utilized. Results require the application of a scaling factor at box 218 representing mastering or normalizing shown in FIG. 13. The algorithm then extracts thread and other thread attributes at box 220. The lighting/modulating strategy during real image collection should be tuned or optimized. This could be as simple as correctly calibrating the intensity of the function generated pulse or as complicated as a synchronization of multiple colored light sources to achieve the gradient needed.

If a three-dimensional Stitch-Modulation is not required at the decision diamond 212, then the algorithm performs edge detection at box 222 and then proceeds to the box 102.

Once the images have been formatted, they are looked at to identify thread defects at box 104 in the manner as discussed above. A cross-section along the thread axis is generated relative to the previously defined coordinate system. The intersection points of the cross-section and the threading lines A, B, C, . . . , H, I in the image are defined. The corresponding linear distances along the image of these points from the reference coordinate system, such as AB, AC, AD, AE, AF, AG, AH, AI, etc., are measured. The thread pitch among different threads is estimated by counting the thread lines or the light of the strips because the distance of four strips defines a pitch. Hence p=BC+CD+DE+EF or p=CD+DE+EF or p=DE+EF+FG+GH, etc. The thread height h is estimated from the theoretical thread profile using the 60° included thread angle. Hence, the thread height for each thread tooth is estimated because the segments BC, DC, and DE are known.

The thread height for cut threads is estimated through equation $h_i=0.5773 \times BC$. For roll form threads the height is estimated by comparing the two segments per tooth, such as BC and DE. If the segments are equal the thread form is uniform. Otherwise, there is some concern with the crest of the rolled thread. In this case, the average thread height is estimated as $h_i=0.289 (BC+DE)$.

The imaging script processes the images and separates the particles in a binary form, ultimately defining all thread lines and defects. The script methodology evaluates the start of the lead thread and other thread features, such as pitch, thread height and defective or missing threads shown.

A clustering threshold is performed at box 106. A sophisticated statistical algorithm is employed to resolve the image into a binary image. In effect, a cluster of the pixels surrounding a central pixel is analyzed. The value of the central pixel based on the statistical analysis of the cluster is converted to either a 0 (black) or a 255 (white). The process extends throughout the entire image.

A binary morphology operation is performed at box 108 that performs an erosion function, i.e., reduces the foreground, to remove very small defects. In effect, the process applies a small particle removal algorithm to filter small defects out of the image. This step may run several times in the algorithm to better clean the image. This minimizes the number of noisy objects in the region of interest to improve the accuracy of the inspection.

An invert binary image operation is performed at box 110. This operation simply changes the individual pixel values of the presented image from those at 0 to 255 to those at 255 to 0. The result is an image that is "reversed" from the input image.

An advanced morphology operation is performed at boxes 112 and 116. This operation removes small defects, removes large objects, removes border objects, fills holes, smoothes feature edges, etc. For example, the fill holes algorithm identifies the part features with cavities intercepting the surface, i.e., crest and flank face, and it filters out their shape by filling up as black to separate them from defects.

An image buffering operation is then performed at box 114. This process simply stores the processed image in a computer memory or in a mass storage device for a later operation.

A math operation step is performed at box 118. This step employs a standard "Exclusive OR" logical operation. The current (source) image and the image stored in the buffer are compared, pixel by pixel, and a third image is created per the "Exclusive OR" standard truth table. The resulting image reveals only the thread lines and defects to be analyzed for conformance to the quality requirements.

A final particle analysis operation is performed at box 120. Within each pre-defined N region of interest, an assessment of thread lines and its X-Y location is made. Finally, all statistical data is generated and processed using statistical software.

The algorithm then defines the rolling thread of interest within rolling threads in the image at box 122 and defines the regions of interest within the cut threads in the image at box 124. The algorithm defines a region of interest for the threads with different rejection criteria at box 126. The algorithm then defines the thread profile within each region of interest at box 128, and classifies the thread defects within each region of interest at a particular X-Y location at box 130.

Once these operations have been performed, the algorithm then goes through several operations for analyzing the threads, including estimating the start of the lead thread and its angular location at box 132, as discussed above. Further, the algorithm generates a histogram of the thread defect sizes for the region of interest and its full surface at box 134. The algorithm also estimates the pitch consistency among the threads in the full surface at box 136. The algorithm also estimates the thread depth and defines the thread crest and root estimates the thread height at box 138.

From all these processes, the algorithm applies evaluation criteria at diamond 140 to determine whether the part should be rejected or accepted. For the parts that are rejected, the defects are marked attributing to part rejection of the surface at box 142 and the part is reevaluated at box 144. For those parts that are accepted, the part is advanced in the next production stage at box 146.

FIG. 10 is a block diagram of a control system 150 integrated into a CNC machine tool 152 for threading holes, showing the control aspects of the process for examining a threaded bore that includes providing improved thread quality. The CNC machine 152 includes a fixture 158 on which a part 154 is mounted. The machine 152 also includes a camera and probe assembly 156 and a moveable table 160. The moveable table 160 is moved by actuators 162 that are part of a machine tool 164. The CNC machine 152 is controlled by a CNC system 166 and an adaptive controller 168. The machine tool 152 will thread a hole and then the threaded hole is either inspected in the same machine by changing the cutting tool in the spindle with the probe assembly 156 or using a separate automatic thread inspection station 178. If the inspection station 178 is used, the camera discussed above is located in the station 178 to provide the inspection. The part will be transferred from the machine 152 to the station 178.

Once the images of the part 154 are taken, the system 150 employs a thread status vision sub-system 170 that determines the location of the lead thread, thread defects and missing threads. The system 150 includes a measured variables sub-system 172 that provides measured variables for the start thread, thread defects and missing thread, and also provides tool condition from a machine status block 174. The system 150 also includes a post process sub-system 176 that includes the automatic thread inspection station 178, an automatic Z-axis distance calculation block 180, an automatic tool inspection block 182 and a status and performance monitoring block 184. The status and performance monitoring block 184 provides signals to the machine status block 174 and a vision system status block 186. A signal processing for monitoring diagnosis block 188 provides signal processing. The status and performance monitor block 184 provides constraint signals, strategy signal and performance index signals to the adaptive controller 168.

The advantages of this invention include that it provides a computer vision-based methodology for non-contact start lead thread and thread profile inspection for threaded bores. The invention also provides a computer non-contact range sensor methodology for start lead thread and thread profile inspection for threaded internal or external features. The invention also provides a complete automated system including a special tool holder as an integral part of the lenses, lighting and camera and the script. The present invention further provides a methodology with the proper decision scheme so that bores are selected based on one of the four quadrants or the actual position of the start thread is located. The invention provides an in-line non-contact gage with feedback to the machining process, and provides a control scheme to monitor the threading process in the machine tool in relation to start lead thread and thread profile.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. An imaging system for imaging a threaded bore in a part, said imaging system comprising:
   a moveable table on which the part is mounted;
   a tool-holder mounted relative to the table;
   a camera mounted to the tool-holder;
   a probe mounted to the tool-holder;
   an optical assembly mounted to an end of the probe opposite to the tool-holder; and
   a controller for controlling the operation of the camera, the tool-holder and the table so that the optical assembly is inserted into the threaded bore in the part to take images of the threaded bore, said camera receiving signals from the optical assembly and providing images of the threaded bore, said controller receiving the images from the camera and converting the images to elongated image slices that are joined together to form a complete image of the bore including a thread line representing threads in the bore, said controller identifying a start location of the threads and/or the profile in the threaded bore.

2. The system according to claim 1 wherein the controller identifies whether the start location of the thread in the bore is at one of four quadrants around a perimeter of the threaded bore or its actual angular location with respect to part coordinates.

3. The system according to claim 1 wherein the controller also determines whether there are defects in the threaded bore from the complete image.

4. The system according to claim 3 wherein the controller determines the profile of the threads including thread pitch, thread height, lead angle, and the size and spacing of crests and valleys of the threaded bore to determine defects.

5. The system according to claim 4 wherein the controller also determined the thread height that requires a stitch-modulated application where the light source is synchronized with the probe insertion speed in the bore.

6. The system according to claim 3 wherein the controller generates a histogram of thread defects.

7. The system according to claim 3 wherein the controller estimates the pitch of crests of the threads in the bore.

8. The system according to claim 1 wherein the controller performs processing on the images including scaling the images, defining regions of interest in the image and identifying surface grey scale lines in the image.

9. The system according to claim 1 wherein the threaded bore is a bore in a cylinder head for a vehicle that accepts a threaded a spark plug.

10. An inspection system for inspecting a threaded bore in a part, said inspection system comprising:
    a probe operable to be incrementally positioned within the bore, said probe including an optical assembly that receives light from inside the threaded bore;
    a camera receiving the light received by the optical assembly and providing images of the bore as the probe is sequentially moved within the bore, each image being an image slice; and
    a controller receiving the images from the camera, said controller unwrapping each image slice to provide an elongated image and joining each elongated image together to provide a complete image of the bore.

11. The system according to claim 10 wherein the controller identifies a start location of a lead thread within the bore from the joined image.

12. The system according to claim 10 wherein the controller also determines whether there are defects in the threaded bore from the complete image.

13. The system according to claim 10 wherein the threaded bore is a bore in a cylinder head for a vehicle that accepts a threaded a spark plug.

14. An inspection system for inspecting a threaded bore in any part such as a cylinder head for a vehicle that accepts a threaded component such as a spark plug, said inspection system comprising:
    a moveable table on which the part is mounted;
    a tool-holder positioned relative to the table;
    a camera mounted to the tool-holder;
    a probe mounted to the tool-holder;
    an optical assembly mounted to an end of the probe opposite to the tool-holder, said camera providing image slices of the bore as the probe moves through the bore; and
    a controller controlling the operation of the system and receiving the image slices from the camera, said controller unwrapping each image slice to provide an elongated image and joining each elongated image together to provide a planer image of the bore, said controller identifying a start location of a lead thread within the bore from the joined image.

15. The system according to claim 14 wherein the controller determines whether there are defects in the threaded bore from the image slices.

16. The system according to claim 15 wherein the controller determines the size and spacing of crests and valleys of the threaded bore to determine defects.

17. The system according to claim 15 wherein the controller generates a histogram of thread defects.

18. The system according to claim 15 wherein the controller estimates the pitch of crests of the threads in the bore.

19. The system according to claim 14 wherein the controller performs processing on the image slices including scaling the image slices, defining regions of interest in the image slices and identifying surface grey scale lines in the image slices.

* * * * *